(12) United States Patent
Bausewein et al.

(10) Patent No.: US 8,241,231 B2
(45) Date of Patent: Aug. 14, 2012

(54) DEVICE, SENSOR, SENSOR ELEMENT AND METHOD FOR MEASURING THE PROFILE OF A SPINAL COLUMN AND FOR MEASURING CHANGES IN THE PROFILE OF THE SPINAL COLUMN

(75) Inventors: Andreas Bausewein, Langenbach (DE); Thomas Bierhoff, Volkmarsen (DE); Dirk David Goldbeck, München (DE); Tobias Happel, Berlin (DE); Hans-Jürgen Schrage, Lippstadt (DE)

(73) Assignee: Siemens Aktiengesellschaft, Munich (DE)

( * ) Notice: Subject to any disclaimer, the term of this patent is extended or adjusted under 35 U.S.C. 154(b) by 946 days.

(21) Appl. No.: 12/225,708

(22) PCT Filed: Mar. 7, 2007

(86) PCT No.: PCT/EP2007/052116
§ 371 (c)(1),
(2), (4) Date: Sep. 29, 2008

(87) PCT Pub. No.: WO2007/110300
PCT Pub. Date: Oct. 4, 2007

(65) Prior Publication Data
US 2009/0234250 A1    Sep. 17, 2009

(30) Foreign Application Priority Data

Mar. 27, 2006  (DE) .......................... 10 2006 014 379
Jun. 21, 2006  (DE) .......................... 10 2006 028 506
Sep. 25, 2006  (DE) .......................... 10 2006 045 138

(51) Int. Cl.
*A61B 5/103* (2006.01)
(52) U.S. Cl. .................................. 600/594; 250/227.14
(58) Field of Classification Search .................. 600/594; 250/227.14
See application file for complete search history.

(56) References Cited

U.S. PATENT DOCUMENTS

| | | | |
|---|---|---|---|
| 3,608,541 A | 9/1971 | Hall | |
| 5,012,819 A | 5/1991 | Marras et al. | |
| 5,143,088 A | 9/1992 | Marras et al. | |
| 5,321,257 A | 6/1994 | Danisch | |
| 6,127,672 A | 10/2000 | Danisch | |
| 2002/0088931 A1* | 7/2002 | Danisch et al. | 250/227.14 |
| 2002/0170193 A1 | 11/2002 | Townsend et al. | |

FOREIGN PATENT DOCUMENTS

| | | |
|---|---|---|
| DE | 690 06 595 T2 | 5/1994 |
| DE | 20 2005 015 889 U1 | 2/2006 |
| WO | 00/68645 | 11/2000 |

OTHER PUBLICATIONS

International Search Report for PCT/EP2007/052116 mailed Jun. 20, 2007.

* cited by examiner

*Primary Examiner* — Max Hindenburg
*Assistant Examiner* — Renee Danega
(74) *Attorney, Agent, or Firm* — Staas & Halsey LLP

(57) ABSTRACT

The profile of the spinal column and changes in the profile of the spinal column are continuously measured during movement along the entire spinal column in all degrees of freedom of its deformation.

23 Claims, 5 Drawing Sheets

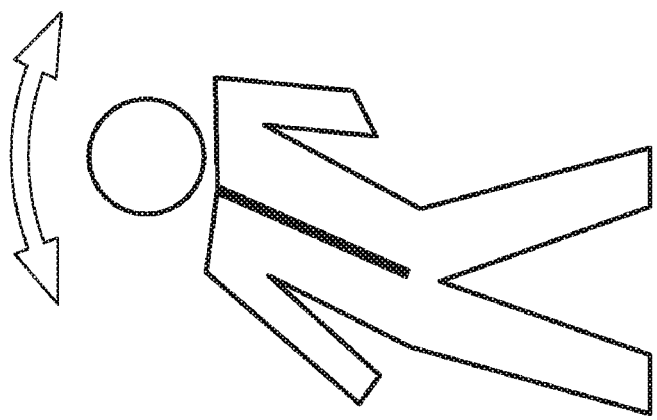
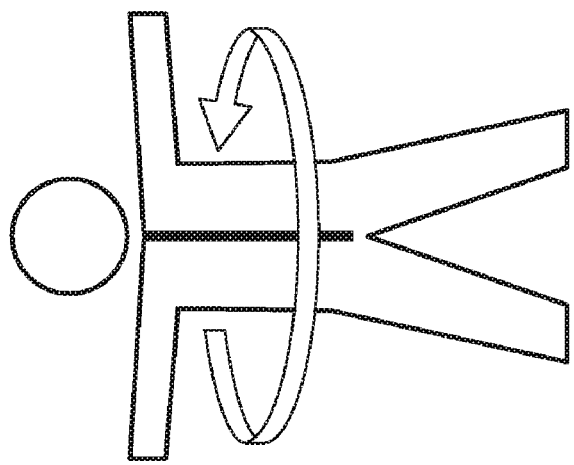
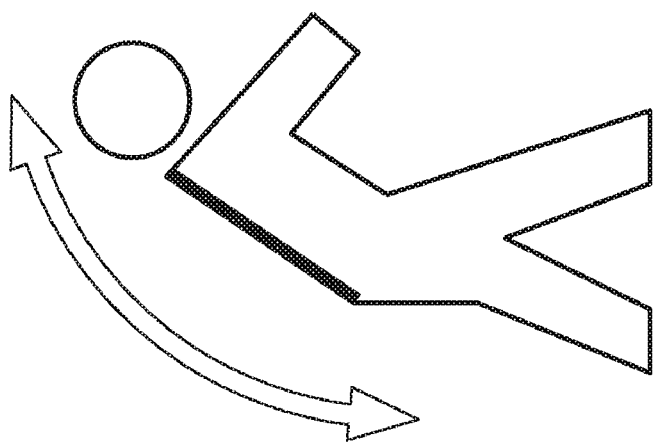

DEVICE, SENSOR, SENSOR ELEMENT AND METHOD FOR MEASURING THE PROFILE OF A SPINAL COLUMN AND FOR MEASURING CHANGES IN THE PROFILE OF THE SPINAL COLUMN

CROSS REFERENCE TO RELATED APPLICATIONS

This application is based on and hereby claims priority to German Application No. 10 2006 014 379.5 filed on Mar. 27, 2006, German Application No. 10 2006 028 506.9 filed on Jun. 21, 2006, and German Application No. 10 2006 045 138.4 filed on Sep. 25, 2006, the contents of which are hereby incorporated by reference.

BACKGROUND

Described below is a device for measuring the profile of a spinal column, a sensor as well as a sensor element for such a device and a method for continuously measuring the profile of the spinal column.

Due to the continuing increase in spinal disorders, for example caused by faulty posture in the workplace, obesity and insufficient mobility of the back muscles due to a lack of movement, the requirement for therapeutic and diagnostic aids is increasing in orthopaedics for identifying and reducing the causes of disease and the resulting consequences for the patient.

Systems currently available on the market for measuring the profile of the spinal column have clear drawbacks. Either the profile of the spinal column is measured in its entirety, but in a static state, or the systems are mobile systems for dynamic measurement, the sensors however only being fastened at specific points along the spinal column and the profile of the spinal column therefore not being able to be measured throughout.

SUMMARY

An aspect is to provide a device in which improved measurement is permitted, as well as a method to provide continuous measurement.

A first subject of this disclosure relates to a device for measuring the profile of the spinal column, which continuously measures the profile of the spinal column and continuously measures the changes to the profile of the spinal column during movement along, in particular, the entire spinal column in all degrees of freedom of its deformation.

The device permits a full, continuous measurement of the profile of the spinal column in the lateral and dorsal direction as well as in torsion both in the static, resting and in the dynamic, moved state.

According to an advantageous embodiment, means for continuously measuring the profile of the spinal column and means for continuously measuring the changes to the profile of the spinal column during movement along, in particular, the entire spinal column in all degrees of freedom of its deformation include at least one common sensor which is sensitive to a deformation in the direction of at least one degree of freedom, and detects at least the part of the spinal column to be measured, as well as an evaluation unit connected to the sensor. In this case, either one sensor may be provided for detecting all degrees of freedom, or separate sensors may be provided for detecting one respective degree of freedom. It is essential in this case that both the continuous measurement of the profile of the spinal column and the continuous measurement of the changes to the profile of the spinal column during movement along, in particular, the entire spinal column in all degrees of freedom of its deformation take place by using the same sensor or the same sensors. This is made possible, amongst other things, by the sensor not only detecting the spinal column at specific points but, for example, extending over the entire part of the spinal column to be detected and thus being able to detect this entire part, in particular with regard to changes to the profile. In this case, it is perfectly conceivable for the spinal column to be detected by being divided into discrete portions, by the sensor preferably extending along the spinal column, relative movements being able to be detected between the individual portions in the direction of all degrees of freedom. As a result, the cost both for attaching suitable means for continuously measuring the profile of the spinal column and the changes to the profile of the spinal column, and for evaluating the sensor data obtained is kept low and at a reasonable level. By the small number of individual sensors, an effective continuous measurement of the profile of the spinal column is possible at rest as well as a measurement of the changes to the profile of the spinal column during movement, as the posture and movement of a spinal column to be measured is not restricted and/or is restricted as little as possible.

Preferably, the sensor which is sensitive to a deformation at least in the direction of one degree of freedom, includes at least one optical waveguide extending over at least one part of the spinal column to be measured, and including at least one bending-sensitive zone relative to a deformation in the direction of at least one degree of freedom, at least one light source radiating a constant light output at a first end of the optical waveguide, as well as at least one receiver measuring the light output incident at a second end of the optical waveguide, the receiver being connected to the evaluation unit. Optical fiber waveguides are provided as sensors which, for example by partial geometric changes in the core-cladding transition zone, are sensitive to bending, which when bending the optical waveguide for example act as interference. The region of an optical waveguide having such an alteration arranged, for example, in the core-cladding transition zone is denoted as the sensitive zone or bending-sensitive zone. If in an optical waveguide with a bending-sensitive zone a constant light output is radiated at the first end of the optical waveguide, for example by an LED (light emitting diode) or a laser light source, such as for example a laser diode, and if the light output is measured at the second end, for example by a photodiode or a phototransistor, the light output measured at the second end alters depending on the bending of the optical waveguide in the region of the sensitive zone. By use of suitable software, the measured data may be transferred into a graphic representation of the profile of the spinal column by taking into account all degrees of freedom of the change to the profile. Optical waveguides with bending-sensitive zones may be arranged to extend along the entire spinal column, in contrast to known sensors. As a result, the profile of the spinal column may be continuously measured, and changes to the profile of the spinal column may also be measured when moving along, in particular, the entire spinal column in all degrees of freedom of its deformation.

The term "constant light output" means, within this disclosure, that the light output radiated in the optical waveguides at the time of measurement is invariable, so that by measuring the incident light output, the light output lost in the region of the bending-sensitive zone may be determined in a qualitative manner at the same time and/or the incident light output directly represents a measurement of the proportion of the light output lost in the bending-sensitive zone. It is, therefore, irrelevant whether the constant light output is continuously radiated in the optical waveguides, i.e. without interruption, or in a pulsed manner at discrete time intervals, at which one respective measurement takes place.

One advantageous embodiment of the device provides that the sensor is divided into a plurality of portions. In this case each portion includes at least one optical waveguide including at least one bending-sensitive zone relative to a deformation in the direction of at least one degree of freedom, for continuously measuring the profile of the spinal column and changes to the profile of the spinal column within the respective portion and/or over adjacent portions. Such a sensor is able to be manufactured at low cost from a plurality of similar sensor elements of any length, each of which includes an optical waveguide having a bending-sensitive zone.

The portions are in this case preferably arranged in succession at least at intervals of adjacent vertebrae of a spinal column, or directly in succession. The spinal column is only able to move between the vertebrae, the vertebrae themselves are rigid. As the portions are arranged at intervals of the vertebrae, it is ensured that every movement of the spinal column, which is made up of relative movements between adjacent vertebrae, may be detected to a sufficient degree.

According to a particularly advantageous embodiment, three optical waveguides are provided with at least one respective bending-sensitive zone for each portion. In this case, one respective optical waveguide including at least one bending-sensitive zone is provided within the portion for measuring one respective degree of freedom, in lateral and dorsal movement as well as in torsion. It is substantially easier to provide bending-sensitive zones on one optical waveguide, which are sensitive to one degree of freedom, than to produce a bending-sensitive zone which is sensitive to a several degrees of freedom or all degrees of freedom. By the use of three optical waveguides, with different respective sensitive zones for torsion, and dorsal and lateral movement all degrees of freedom may be detected at a low constructional cost.

A second subject of this disclosure relates to a sensor for continuously measuring the profile of the spinal column and changes to the profile of the spinal column during movement along the entire spinal column in all degrees of freedom of its deformation. The sensor includes at least one optical waveguide extending over at least one part of the spinal column to be measured, including at least one bending-sensitive zone relative to a deformation in the direction of at least one degree of freedom, at least one light source radiating a constant light output at a first end of the optical waveguide, as well as at least one receiver measuring the light output incident at a second end of the optical waveguide. Optical waveguides with bending-sensitive zones may be arranged to extend along the entire spinal column, in contrast to known sensors. As a result, the profile of the spinal column may be continuously measured, in addition to changes to the profile of the spinal column during movement along, in particular, the entire spinal column in all degrees of freedom of its deformation.

The sensor may include sensor elements arranged directly in succession or at least at intervals of adjacent vertebrae of a spinal column, which are respectively provided for continuously measuring the profile of the spinal column and changes to the profile of the spinal column, within a portion formed by the respective sensor element, or between adjacent portions. Each of the sensor elements includes at least one optical waveguide including at least one bending-sensitive zone relative to a deformation in the direction of at least one degree of freedom. In the sensor, one respective light source radiating a constant light output at a first end of the respective optical waveguide is provided for each optical waveguide, as well as at least one receiver measuring the light output incident at a second end of the respective optical waveguide.

Preferably, the sensor elements are arranged on a common elastically expandable strip-shaped support material, at least within the mobility of the entire spinal column in all its degrees of freedom of its deformation. For example foam material or plaster material are suitable as expandable support material. So that the optical waveguides of the sensor and/or of the sensor elements may follow a resilient expansion of the support material, the optical waveguides are, for example, arranged in a meandering manner on the support material. It is also conceivable to obtain a longitudinal flexibility by the optical waveguides being fastened partially to support plates which have a high tensile strength but which are flexible, which in turn are arranged on the strip-shaped support material. The optical waveguides extend between the support plates in arcuate expansion loops. A sensor of such a construction is also denoted hereinafter as a sensor strip.

The sensor may include suitable means for protecting the strip-shaped support material from damage by overexpansion. Such means may, for example, be tension straps arranged on both sides on the longitudinal sides of the strip-shaped support material, which are tensioned beyond a definable expansion of the support material and thus prevent a further expansion of the support material.

A third subject of this disclosure relates to a sensor element for use in a sensor described above. A sensor element includes at least one optical waveguide extending over a part of the spinal column to be measured, and including at least one bending-sensitive zone relative to a deformation in the direction of at least one degree of freedom. Preferably, one respective optical waveguide is provided for each degree of freedom, each optical waveguide including at least one respective bending-sensitive zone designed for deformation in the direction of the respective degree of freedom. Determining and differentiating the deformations and/or changes to the profile and their configuration in a specific portion of the optical waveguide requires an optical waveguide having a sensitive zone of appropriate configuration for each degree of freedom to be considered of the change to the profile.

By a suitable combination of optical waveguides with respective sensitive zones designed for the measurement of a specific degree of freedom, overall a sensor element is produced which allows the measurement of changes to the profile in the degrees of freedom relevant for a spinal column. A sensor element is preferably provided for measuring a spinal column in the degrees of freedom, in dorsal and lateral movement and in torsion, and includes a total of three optical waveguides with at least one respective bending-sensitive zone designed for the measurement of the respective degree of freedom. If the sensitive zones of the combined optical waveguides of the sensor element extend over the same portions along the spinal column, a change to the profile in this portion may be measured relative to all degrees of freedom considered.

If a plurality of such sensor elements are combined such that their sensitive zones are in succession, a sensor is obtained by which the changes to the profile may be determined in a plurality of portions formed by the sensor elements in all degrees of freedom considered. As a result, a sensor described above and including a plurality of sensor elements is obtained. By determining the changes to the profile in the sensitive portions of the individual sensor elements by measurement, the change to the profile of an object may be completely and seamlessly determined over larger portions. By use of suitable software, the measured data may be transferred from the sensitive zones of the interlinked sensor elements into a graphic representation of the profile of the spinal column by taking into account all degrees of freedom of the change to the profile.

The bending-sensitive zones of an optical waveguide of a sensor element may, for example, be formed by partial geometric changes in the core-cladding transition zone. The physical principle used here is that the partial interference of the optical waveguide in the core-cladding transition zone causes a loss of the light output in the optical waveguide in the sensitive zone. A bending of the optical waveguide in the region of the sensitive zone increases or reduces the loss of light output. The partial geometric changes in the core-cladding transition zone may, for example, be produced by mechanical machining of the optical waveguide in the region of the core-cladding transition zone thereof. According to the degree of freedom to be measured, the bending-sensitive zones of the optical waveguide are arranged on a specific peripheral position of the optical waveguide. The partial geometric changes may, for example, depending on the bending of the optical waveguide, include indentations in the core-cladding transition zone influencing the scattering behavior and reflexion behavior in the interior of the optical waveguide.

It is important to stress that, in principle, it is also conceivable to use a common optical waveguide with bending-sensitive zones for torsion and movement in the lateral and dorsal direction, in combination with light polarized in suitable planes and detection of the incident light output specific to the polarization plane. It is also conceivable to arrange bending-sensitive zones on the optical waveguide which are wavelength-specific as well as to use a light source which radiates a constant light output at different wavelengths, and to evaluate the absorbed light output in a wavelength-specific manner.

It is also important to stress that, instead of radiating a constant light output at a first end into an optical waveguide and undertaking a measurement of the incident light output at a second end of the optical waveguide, it is generally within the scope of this disclosure to carry out the radiation and measurement at the same end and to reflect the radiated light at the opposing end by suitable means, or as an alternative to allow the light to emerge and only measure the backscattering.

A fourth subject of this disclosure relates to a method for continuously measuring the profile of the spinal column as well as changes to the profile of the spinal column during movement along the entire spinal column in all degrees of freedom of its deformation. The method includes:

arranging at least one optical waveguide with at least one bending-sensitive zone along the spinal column relative to at least one degree of freedom to be measured, radiating a specific light output into the optical waveguide at a first end of the optical waveguide, measuring the incident light output at a second end of the optical waveguide, and determining the deformation of the optical waveguide and thus the spinal column by comparing the incident light output with the radiated light output.

For arranging the at least one optical waveguide with at least one bending-sensitive zone along the spinal column it is conceivable initially to divide the spinal column into a plurality of portions to be measured and then to arrange one respective sensor element including at least one optical waveguide with at least one sensitive zone for a degree of freedom to be measured, per portion along the spinal column.

In this case, for dividing the spinal column into portions and for arranging one respective sensor element per portion, a number of optical waveguides corresponding at least to the number of portions may be fastened to a support strip, the individual optical waveguides respectively including in a specific portion at least one bending-sensitive zone, and subsequently to fasten the support strip with the optical waveguides arranged thereon along the spinal column to be measured.

Preferably, three respective optical waveguides are provided for measuring one respective degree of freedom within a portion.

The bending-sensitive zones of the optical waveguides are preferably produced in the respective portions by mechanical machining of the optical waveguides.

According to an advantageous development of the method, the deformation of the spinal column is determined by comparing the incident light output with the radiated light output in a time-discrete manner and the deformations thus determined are detected and, for example, stored over a specific time period for subsequent evaluation.

BRIEF DESCRIPTION OF THE DRAWINGS

These and other aspects and advantages will become more apparent and more readily appreciated from the following description of the exemplary embodiments, taken in conjunction with the accompanying drawings of which:

FIG. 2 is a schematic view of the degree of freedom of spinal column movement.

DETAILED DESCRIPTION OF THE PREFERRED EMBODIMENT

Figure 1A:
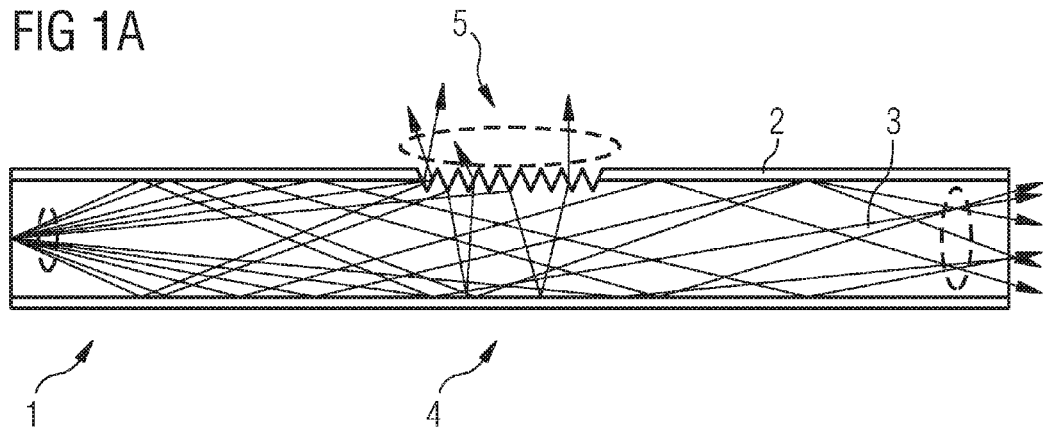
FIGS. 1A-1c are cross-sectional views of the effect of a partial geometric change of an optical waveguide in the core-cladding transition zone thereof on the change of the light output transmitted when bent.

Reference will now be made in detail to the preferred embodiments, examples of which are illustrated in the accompanying drawings, wherein like reference numerals refer to like elements throughout.

A principal feature of this disclosure is to be able to carry out continuously a measurement of the profile as well as changes to the profile of a spinal column in the resting and in the mobile state, i.e. continuously in all its degrees of freedom of movement by a suitable device. To this end a device is provided which includes means preferably in the form of suitable sensors both for continuously measuring the spinal column profile and for continuously measuring the changes to the profile of the spinal column during movement along the entire spinal column in all degrees of freedom of its deformation.

Optical fiber waveguides 1 are provided as sensors which, as shown in FIG. 1, by partial geometric changes 5 in the core-cladding transition zone are sensitive to bending which act on the transmission behavior of light as interference. The region of an optical waveguide 1 with such a change 5 in the core-cladding transition zone is denoted as a sensitive zone 4.

Figure 1B:
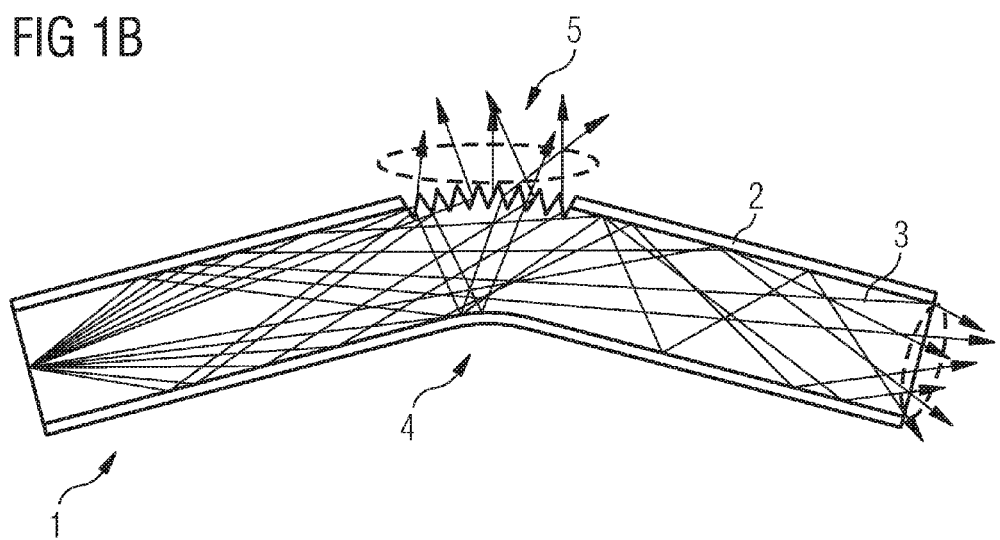
Figure 1C:
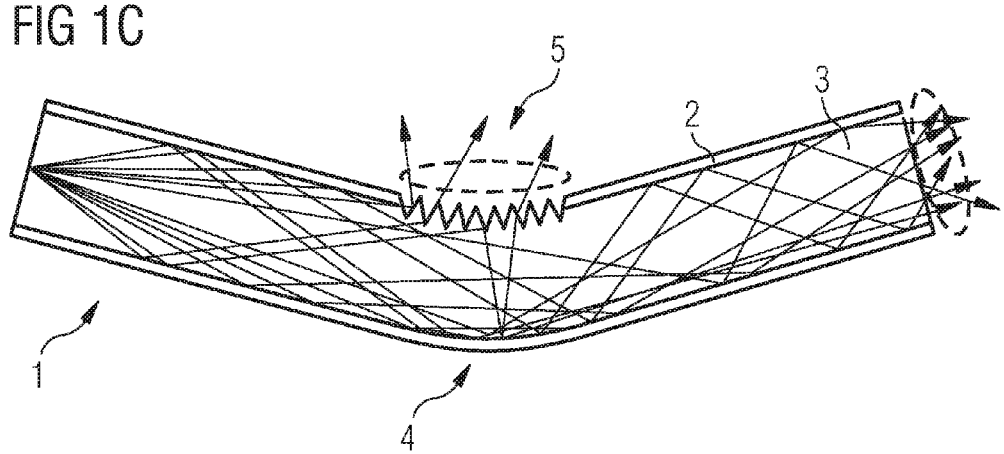

If at a first end of an optical waveguide 1 with a sensitive zone 4, for example with an LED or laser diode, a constant light output is radiated and at a second end the incident light output is, for example, measured by a photodiode or a phototransistor the light output measured at the second end is thus altered depending on the bending of the optical waveguide 1 in the sensitive zone 4. The partial interference 5 of the optical waveguide 1 in the transition between the core 3 and the cladding 2 causes a loss of light output in the optical waveguide 1 in the sensitive zone 4. A bending of the optical waveguide 1 in the region of the sensitive zone 4 increases (FIG. 1*c*) or reduces the loss of the light output (FIG. 1*b*). FIG. 1*a* shows the optical waveguide 1 in the extended state.

By a suitable arrangement and shape of the sensitive zone each change to the profile of the optical waveguide in the region of the sensitive zone may be determined by measuring the changing light output. Measurable changes to the profile of the optical waveguide are (FIG. 2):

so-called dorsal movement, which includes vertical bending in both directions (FIG. 2*a*), torsion (FIG. 2*b*), and so-called lateral movement which includes horizontal bending in both directions (FIG. 2*c*).

In order to be able to detect the profile and the changes to the profile of a spinal column in all degrees of freedom of its movement, the sensor extends at least over the part of the spinal column to be measured. The sensor is in this case divided into a plurality of portions, each portion including at least one optical waveguide having at least one bending-sensitive zone relative to deformation in the direction of at least one degree of freedom, for continuously measuring the profile of the spinal column and changes to the profile of the spinal column within the respective portion and/or over adjacent portions.

Determining and differentiating the changes to the profile and their configuration in a specific portion of the optical waveguide requires an optical waveguide with a sensitive zone of appropriate configuration, for each degree of freedom considered in the change to the profile. By a suitable combination of optical waveguides with sensitive zones respectively designed for the measurement of a specific degree of freedom, overall a sensor element is produced which allows the measurement of the change to the profile in the three degrees of freedom considered here. If the sensitive zones of the combined optical waveguides extend over the same portions along the sensor element, a change to the profile in this portion may be measured relative to all degrees of freedom considered. Three optical waveguides with at least one respective bending-sensitive zone are thus arranged per portion for detecting all degrees of freedom, one respective optical waveguide including at least one bending-sensitive zone being provided within the portion for measuring one respective degree of freedom, in lateral and dorsal movement and in torsion.

If a plurality of such sensor elements are combined such that their sensitive zones are in succession, a sensor is obtained by which the changes to the profile may be determined in a plurality of portions formed by the sensor elements in all degrees of freedom considered. By determining the changes to the profile in the sensitive portions of the individual sensor elements by measurement, the change to the profile of an object such as a spinal column may be completely and seamlessly determined over larger portions.

By use of suitable software, the measured data may be transferred from the sensitive zones of the interlinked sensor elements into a graphic representation of the sensor profile by considering all degrees of freedom in the change to the profile.

By the use of a sensor described above, having sensor elements for measuring the profile and changes to the profile of a spinal column, the spinal column is divided into a plurality of portions to be measured, predetermined by the sensor elements, each portion being able to be individually measured by a suitable sensor element via the respective sensitive zones in all directions of movement.

For producing a corresponding sensor, a corresponding number of optical waveguides are fastened preferably parallel or in a meandering path on a support strip formed of a strip-shaped support material, and respectively made to be sensitive to bending in a specific portion along the spinal column by mechanical machining. In this case, one respective optical waveguide is provided per portion for each direction of movement, corresponding to three respective optical waveguides per portion, and mechanically machined in this portion accordingly on its surface.

The support strip with the optical waveguides arranged thereon, which are partially sensitive to bending as a result of the sensitive zones, is fastened by suitable connecting materials, such as for example an adhesive strip or a plaster to the back via the spinal column of a patient.

The optical waveguides guided on the support strip are coupled to transmission and receiver components, such as for example LEDs and photodiodes. Transmission and receiver components are located in a light-impermeable housing.

An evaluation unit also arranged in this housing including a suitable electronics unit detects in a time-discrete manner the change to the analogue signal of the light output on the receiver element, depending on the configuration of the movement in the sensitive zone of the optical waveguide at constant light output of the transmission component and stores the measured analogue values converted into digital data for subsequent analysis.

By using suitable additional hardware and software, a continuous dynamograph of the spinal column with regard to the type of movement and configuration of the movement may be characterized by a time period to be determined and graphically represented.

The resulting information about the dynamics and the loading of the spinal column associated therewith over a specific time period, may be used by a therapist or doctor carrying out treatment as essential decision aids when establishing suitable preventative and therapeutic measures for the patient.

In order to be able to use the above-disclosed sensor principle for measuring the movement on the spinal column, specific technological requirements have to be fulfilled. These are:

longitudinal flexibility of the sensor strip. When the back is curved by inclining the upper body, the length of the back increases by approximately 15-20% relative to the stretched-out back length. A sensor fastened via the spinal column for measuring the spinal column may not be altered in its position on the back. Additionally, the extension of the back has to be able to be transmitted to the sensor, also denoted as a sensor strip, due to the support strip with the bending-sensitive optical waveguides arranged thereon and the sensor as a result behaves flexibly in the longitudinal direction.

configuration of the sensitive zones on the optical waveguides. In order to be able to detect partially the types of movement occurring on the spinal column, in dorsal and lateral movement as well as in torsion (FIG. 2) via the sensor elements, the sensitive zones have to be configured differently on the optical waveguides, i.e. the surfaces of the optical waveguides of the sensor are machined in a variable manner, for example mechanically machined. Via the three sensitive zones of a sensor element arranged in three optical waveguides, of which one of each is provided per sensor element for each type of movement, the three movement directions are ultimately intended to be able to be detected independently of one another in their configuration.

protection of the optical waveguides from mechanical loading. The optical waveguides of the sensor strip fastened to the back have to be protected against mechanical loading and damage which could affect or disrupt the sensor signal.

protection against overexpansion of the sensor strip. In spite of the longitudinal flexibility of the sensor strip an overexpansion has to be avoided by suitable measures.

The solutions according to the aforementioned technological requirements are disclosed below.

Figure 3:
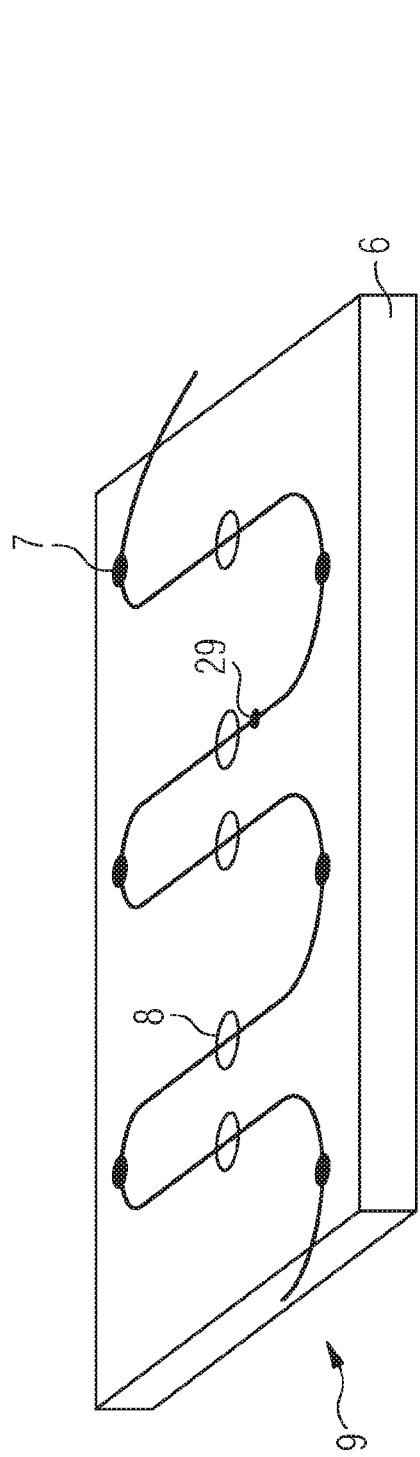
FIG. 3 is a perspective view of a sensor including an elastically deformable strip-shaped support material, a longitudinal flexibility of the sensor strip being achieved by a meandering arrangement of the optical waveguides.
Figure 4:
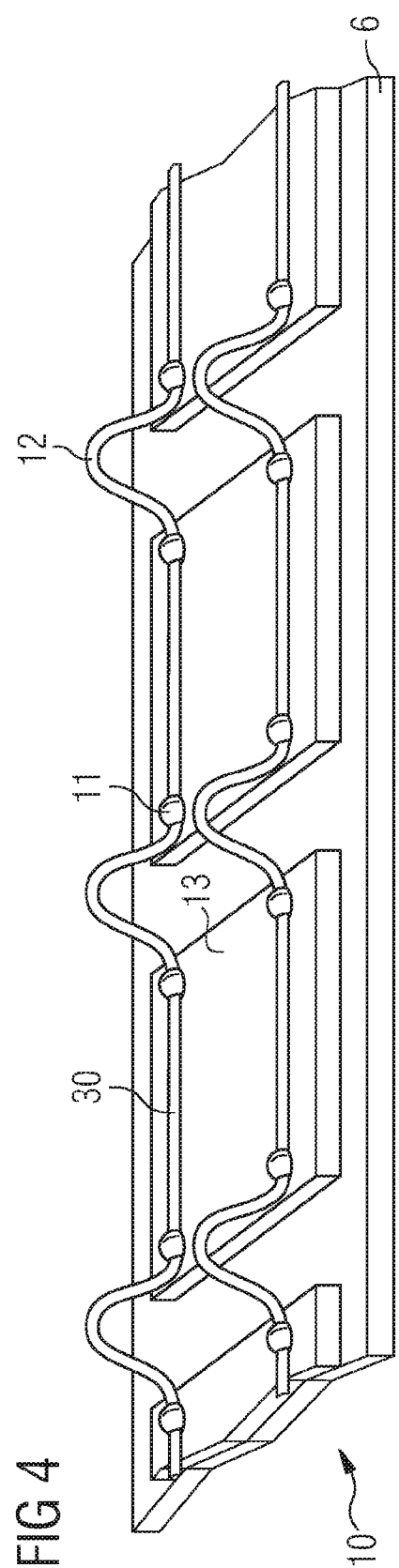
FIG. 4 is a perspective view of a sensor including an elastically deformable strip-shaped support material, a longitudinal flexibility of the sensor strip being achieved by expansion loops with a parallel arrangement of the optical waveguides.

In order to allow the longitudinal flexibility of the sensor strip without mechanically loading the optical waveguide, in principle two variants are conceivable:

a) longitudinal flexibility of the sensor strip 9 by a meandering arrangement of the optical waveguides 29 (FIG. 3). The optical waveguides 29 are laid out in a meandering manner according to FIG. 3 on an expandable, strip-shaped support material 6, and fixed at specific points such that the subsequently unfixed optical waveguide portions alter their position between the possible fixing points 7 on the edge of the support material 6 or the fixing points 8 in the longitudinal axis of the support material 6 during expansion of the support material 6, and thus follow the movement of expansion of the support material 6, without being subjected to mechanical stress or loading which could act on the transmission behavior of the optical waveguides 29. In a sensor strip 9 the sensitive zones are introduced or arranged depending on the type of movement to be detected at appropriate unfixed points of the optical waveguide 29.

b) longitudinal flexibility of the sensor strip 10 by expansion loops with a parallel arrangement of the optical waveguides 30 (FIG. 4). On an expandable, strip-shaped support material 6 according to FIG. 4, support plates 13 made of a material which has a high tensile strength but which is flexible, for example a plastics material such as PET film or Mylar film, are partially fastened to one another at fixed intervals. The optical waveguides 30 are fixed to the support plates 13 in a suitable manner. The fixing takes place by securing the optical waveguides to the fixing points 11. In the region of the intervals between the support plates 13, the optical waveguides 30 are laid out in expansion loops 12. The sensitive zones of the optical waveguides 30 are located respectively in the regions of the support plates 13 having a high tensile strength, as in this case only the type of movement, not the expansion of the sensor strip 10, is intended to have an effect on the sensitive zone of the optical waveguide 30. The expandable support material 6 absorbs the longitudinal tensile load on the sensor strip 10. In this case, the optical waveguide 30 fastened to the support plates 13 is not expanded but by altering the bending radius in the expansion loop 12 is adapted to the longitudinal extension of the sensor strip 10.

Foam material or plaster material are suitable, for example, as expandable support material 6, both for the sensor strip 9 (FIG. 3) and for the sensor strip 10 (FIG. 4). The fixing of the optical waveguides 29, 30 at the fixing points 7, 8, 11 may, for example, take place by suitable adhesives or polymer sealing materials.

The sensitive zones of the optical waveguides have to be mechanically machined according to one of the three types of movement to be determined, dorsal movement, lateral movement and torsion (FIG. 5). To this end, with an optionally parallel or meandering arrangement of an optical waveguide bundle 17 including three optical waveguides 14, 15, 16, the mechanical machining of the individual optical waveguides 14, 15, 16 has to be arranged at different positions on the surface of the optical waveguides 14, 15, 16. The optical waveguide bundle 17 is, for example, arranged on an expandable, strip-shaped support material 6. A portion of the support material 6 including such an optical waveguide bundle 17 and/or the sensitive zones thereof corresponds in this case to a sensor element. A plurality of optical waveguide bundles 17 arranged successively on a support material 6, such that the sensitive zones of the optical waveguide bundle 17 are directly in succession, corresponds to a sensor and/or sensor strip made up of a plurality of sensor elements.

a) a dorsal movement A takes place in the vertical plane of the sensor strip. In order to obtain a sensitivity of an optical waveguide 14 of the optical waveguide bundle 17 in this plane, as shown in FIG. 5 surface treatments in the form of partial geometric changes in the region of the core-cladding transition zone of the optical waveguide 14 are carried out at a peripheral position on the upper face o of the positioned optical waveguide 14.

b) a torsional movement B takes place in the horizontal plane of the sensor strip as a twisting of the sensor strip. Thus a movement takes place in both directions of the horizontal plane which has to be detected in its entirety by the sensitive zone. To achieve a sensitivity of an optical waveguide 15 of the optical waveguide bundle 17 in this plane, surface treatments must be carried out in the form of partial geometric changes in the region of the core-cladding transition zone of the optical waveguide 15 at a peripheral position on the upper face o and lower face u of the positioned optical waveguide 15, as FIG. 5 shows.

c) a lateral movement C takes place in the horizontal plane of the sensor strip. To achieve a sensitivity of an optical waveguide 16 of the optical waveguide bundle 17 in this plane the surface treatments in the form of partial geometric changes in the region of the core-cladding transition zone of the optical waveguide 16 must be carried out at a peripheral position on the side s of the positioned optical waveguide 16, as FIG. 5 shows.

Figure 5A:
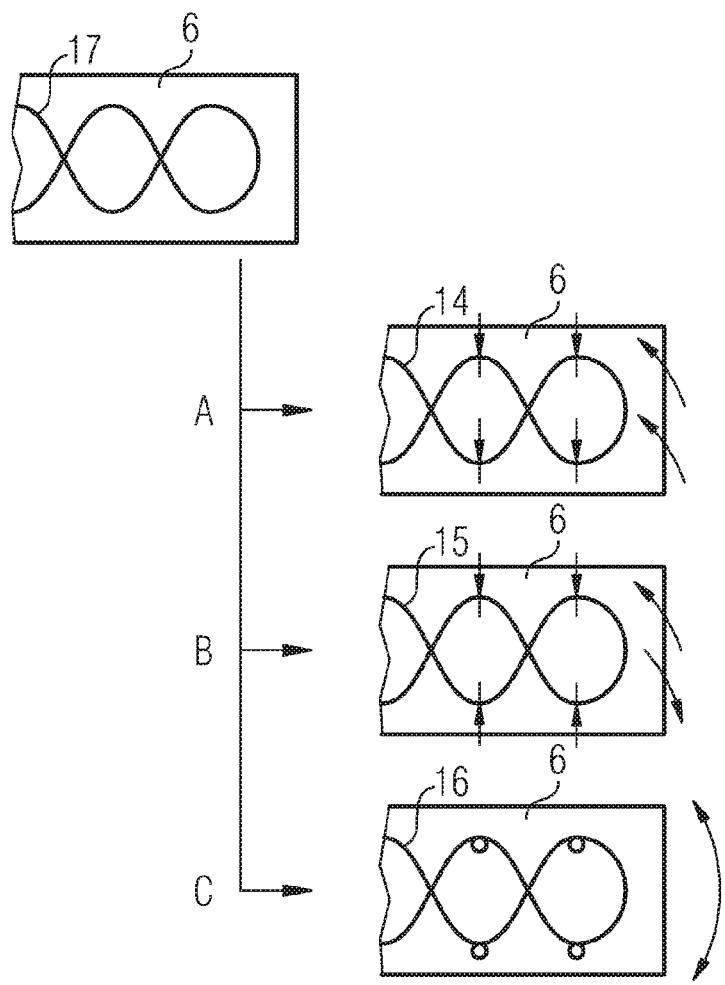
FIG. 5A illustrates a configuration of sensitive zones on optical waveguides.
Figure 5B:
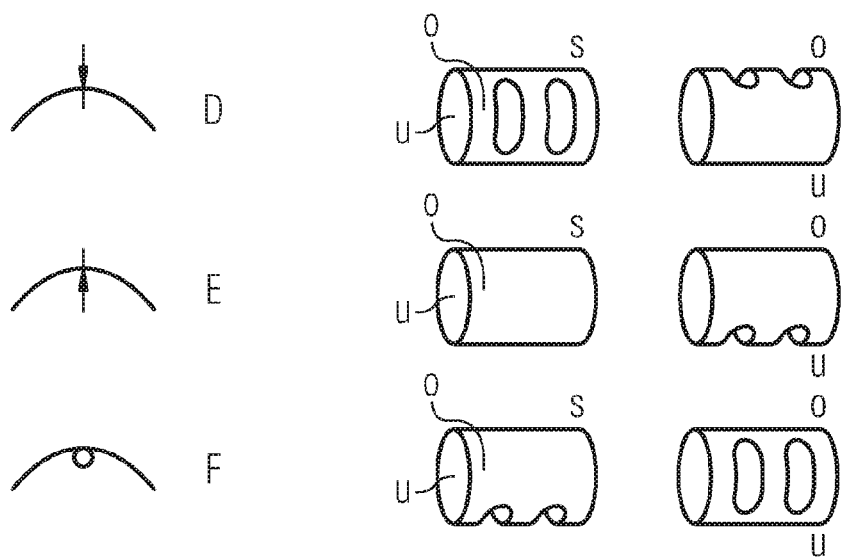
FIG. 5B illustrates perspective and schematic views of a configuration of sensitive zones on optical waveguides.

The arrangement of the partial geometric changes to the respective peripheral position of the optical waveguides 14, 15 and 16 is illustrated in FIG. 5 symbolically by the symbols D, E, F. In this case, FIG. 5b) serves as a key which indicates the treatments to be carried out accordingly at the positions of the optical waveguides 14, 15, 16 at the respective peripheral positions provided in FIG. 5a) for the three types of movement, dorsal movement A, torsional movement B and lateral movement C. In this case, the symbol D indicates a treatment of an optical waveguide on its upper face o, so that on its upper face o a partial geometric change occurs. The symbol E indicates a treatment of an optical waveguide on its lower face u, so that on its lower face u a partial geometric change occurs. The symbol F indicates a treatment of the optical waveguide at its sides s, so that at its sides s a partial geometric change occurs. The corresponding peripheral positions are in this case shown again in detail to the right of the respective symbol.

In spite of desired longitudinal flexibility of the sensor strip, an overexpansion has to be avoided by suitable measures.

Figure 6:
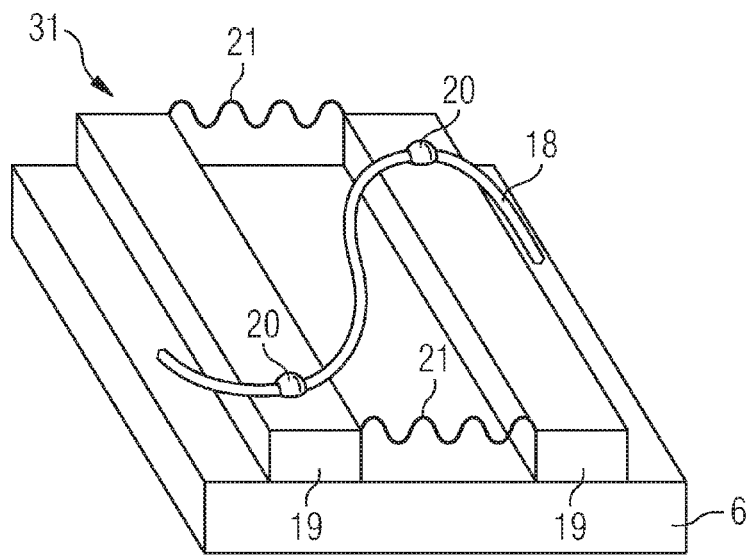
FIG. 6 is a perspective view of a detail of a sensor strip provided with protection against longitudinal overexpansion.

A conceivable solution for a sensor strip 31 protected against overexpansion, is to fix the optical waveguides 18 as shown in FIG. 6 to ribs 19 made of a rigid material, such as a plastics material, at specific points on fixing points 20 on the ribs 19. The ribs 19 are, for example, connected to one another by tension straps 21 arranged on both sides, whereby a limit to the longitudinal expansion of the expandable strip-shaped support material 6 is achieved. The optical waveguide 18 is, as a result, protected from mechanical tensile loading which may lead to the alteration of the optical transmission behavior and thus to the invalidation of the sensor signal.

A further possibility for protecting the optical waveguide 18 against longitudinal overexpansion is to use a flexible support material 6 with a limited expansion.

Additionally, the optical waveguides of the sensor strip fastened to the back have to be protected against mechanical loading and damage, which affect or interfere with the sensor signal.

Figure 7:
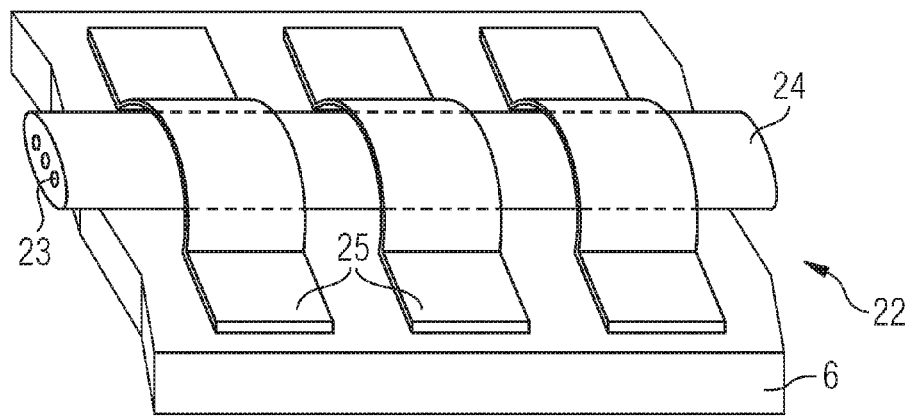
FIG. 7 is a perspective view of a sensor strip provided with protection against compressive loading.

To this end, in the sensor 22 shown in FIG. 7, an optical waveguide bundle 24 including optical waveguides 23, with loops 25 made of a rigid material, which fix the optical waveguide bundle 24 to an expandable, strip-shaped support material 6, is protected from mechanical loading, such as for example compression.

Figure 8:
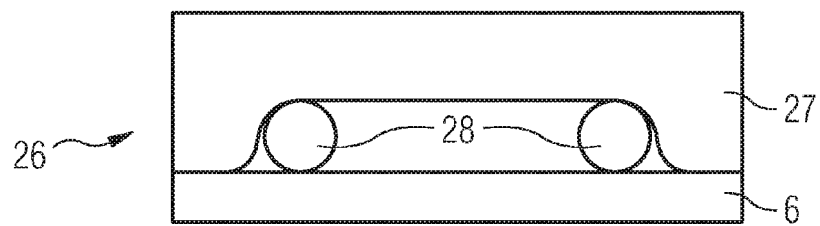
FIG. 8 is a schematic view of a sensor strip which is protected by a protective layer relative to mechanical loading.

The sensor 26 shown in FIG. 8 in cross section is protected by a flexible protective layer 27 from mechanical loading. The protective layer 27 may, for example, be produced from the same material as the support material 6. The protective layer 27 is fastened to the support material 6, for example by bonding, such that the optical waveguides 28 are embedded completely between the support material 6 and the protective layer 27. The support material 6 and the protective layer 27 are able to expand and be compressed to the same extent. Instead of individual optical waveguides, one or more optical waveguide bundles may also be arranged under the protective layer 27.

It is important to stress that the sensor strips 9, 10, 22, 26 and 31 shown in FIGS. 3, 4, 6, 7 and 8 for a device according to the invention mentioned in the introduction, represent suitable means both for continuously measuring the spinal column profile and for continuously measuring the changes to the profile of the spinal column during movement along the entire spinal column in all degrees of freedom of its deformation.

The system also includes permanent or removable storage, such as magnetic and optical discs, RAM, ROM, etc. on which the process and data structures of the present invention can be stored and distributed. The processes can also be distributed via, for example, downloading over a network such as the Internet. The system can output the results to a display device, printer, readily accessible memory or another computer on a network.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV*, 358 F3d 870, 69 USPQ2d 1865 (Fed. Cir. 2004).

The invention claimed is:

1. A device for measuring a profile of a spinal column, comprising:
   one or more sensors each divided into one or more sensor element portions to continuously measure the profile of the spinal column; and
   an electronic change measurement evaluator configured to connect to a sensor and to continuously measure changes to the profile of the spinal column during movement along the spinal column in degrees of freedom of deformation of the spinal column,
   wherein with a plurality of the sensors, said sensors with respective sensor element portions thereof arranged such that the respective sensor element portions of the sensors are in succession of each other at intervals of adjacent vertebrae of the spinal column.

2. The device as claimed in claim 1, wherein at least one of said sensor element portions is sensitive to a deformation in a direction of at least one degree of freedom, that detects at least part of the spinal column to be measured.

3. The device as claimed in claim 1, wherein a sensor element portion comprises:
   at least one optical waveguide extending over at least one part of the spinal column to be measured, having at least one bending-sensitive zone relative to a deformation in a direction of at least one degree of freedom;
   at least one light source radiating a constant light output at a first end of said at least one optical waveguide; and
   at least one receiver measuring output light incident at a second end of said at least one optical waveguide, said receiver being connected to the evaluator.

4. The device as claimed in claim 1, wherein each sensor element portion includes at least one optical waveguide having at least one bending-sensitive zone relative to a deformation in a direction of at least one degree of freedom, for continuously measuring the profile of the spinal column and changes to the profile of the spinal column within a respective sensor element portion and/or over adjacent sensor element portions.

5. The device as claimed in claim 4,
   wherein each of the optical waveguides has at least one bending-sensitive zone within a respective sensor element portion for measuring one respective degree of freedom, in lateral and dorsal movement as well as in torsion.

6. A sensor that is part of a device for continuously measuring a profile of a spinal column and changes to the profile during movement along the spinal column in degrees of freedom of deformation of the spinal column, said sensor comprising:
   one or more sensors each divided into one or more sensor element portions to continuously measure the profile of the spinal column; and
   an electronic change measurement evaluator configured to connect to the sensor and to continuously measure changes to the profile of the spinal column during movement along the spinal column in degrees of freedom of deformation of the spinal column,
   wherein with a plurality of the sensors, said sensors with respective sensor element portions of thereof arranged such that the respective sensor element portions of the sensors are in succession of each other at intervals of adjacent vertebrae of the spinal column.

7. The sensor as claimed in claim 6, wherein each sensor includes:

at least one optical waveguide segment having at least one bending-sensitive zone relative to a deformation in a direction of at least one degree of freedom;

at least one light source radiating a constant light output at a first end of the optical waveguide segment; and at least one receiver measuring the output light incident at a second end of the optical waveguide segment.

8. The sensor as claimed in claim 7, further comprising a common elastically expandable strip-shaped support material on which said sensors are arranged and having mobility corresponding to the spinal column in the degrees of freedom of deformation thereof.

9. The sensor as claimed in claim 8, wherein the optical waveguide segments are arranged in a meandering manner on said support material.

10. The sensor as claimed in claim 8, further comprising support plates, having a high tensile strength but which are flexible, arranged on said strip-shaped support material, on which the optical waveguide segments are fastened and are arranged extending between adjacent support plates in arcuate expansion loops.

11. The sensor as claimed in claim 8, further comprising a protection mechanism to protect the strip-shaped support material from overexpansion.

12. The sensor as claimed in claim 11, wherein said protection mechanism includes tension straps arranged on both sides along longitudinal sides of said strip-shaped support material and tensioned beyond a definable expansion of said strip-shaped support material and thus prevent a further expansion of said strip-shaped support material.

13. A sensor element for use in a sensor that is part of a device for continuously measuring a profile of a spinal column and changes to the profile during movement along the spinal column in degrees of freedom of deformation of the spinal column, comprising:

at least one optical waveguide to extend over a part of the spinal column to be measured and having at least one bending-sensitive zone formed by partial geometric changes in a core-cladding transition zone and relative to a deformation in a direction of at least one degree of freedom, wherein the optical waveguide has an interior and the partial geometric changes depending on a bending of the optical waveguide includes indentations in the core-cladding transition zone influencing scattering behavior and reflection behavior in the interior of the optical waveguide.

14. The sensor element as claimed in claim 13, further including one respective optical waveguide for each degree of freedom, each optical waveguide having at least one respective bending-sensitive zone designed for deformation in a respective direction of a respective degree of freedom.

15. The sensor element as claimed in claim 14, wherein the sensor element is provided for measuring a spinal column in the degrees of freedom, in dorsal and lateral movement and in torsion, and wherein the sensor element includes three optical waveguides with at least one respective bending-sensitive zone measuring the respective degree of freedom.

16. The sensor element as claimed in claim 13, wherein the partial geometric changes in the core-cladding transition zone is produced by mechanical machining of the respective optical waveguide in a region of the core-cladding transition zone thereof.

17. The sensor element as claimed in claim 16, wherein the bending-sensitive zone of the respective optical waveguide is arranged on a peripheral position thereof.

18. A method of using one or more sensors and an electronic change measurement evaluator configured to connect to the sensors for continuously measuring a profile of a spinal column and changes to the profile of the spinal column during movement along the spinal column in degrees of freedom of deformation of the spinal column, comprising:

dividing each sensor into one or more sensor element portions to continuously measure the profile of the spinal column, wherein with a plurality of the sensors, said sensor with respective sensor element portions thereof arranged such that the respective sensor element portions of the sensors are in succession of each other at intervals of adjacent vertebrae of the spinal column.

19. The method as claimed in claim 18, further comprising:

arranging at least one optical waveguide with a bending-sensitive zone for a sensor element portion, wherein the optical waveguide is configured to receive light radiated into the optical waveguide to measure incident light output from the optical waveguide, and a deformation of the spinal column is determinable by comparing the incident light output with the light radiated into the optical waveguide.

20. A method as claimed in claim 19, wherein said determining the deformation of the spinal column includes comparing the incident light output with the light radiated into the optical waveguide in a time-discrete manner, and wherein said method further comprises storing the deformations thus determined.

21. A method as claimed in claim 18, further comprising fastening the sensors to a support strip.

22. A method as claimed in claim 21, wherein three respective sensors with optical waveguides having a bending-sensitive zone are provided for measuring one respective degree of freedom within each portion along the spinal column.

23. A method as claimed in claim 22, wherein the bending-sensitive zones of the optical waveguides are produced by mechanical machining of the optical waveguides.

* * * * *